(12) United States Patent
Simonson

(10) Patent No.: US 12,324,743 B1
(45) Date of Patent: Jun. 10, 2025

(54) METHOD AND APPARATUS FOR PLACEMENT OF A VERTEBRAL BODY REPLACEMENT DEVICE INTO A TRANSCORPOREAL VOID DURING A SURGICAL OPERATION ON THE CERVICAL PORTION OF THE SPINE

(71) Applicant: Robert E. Simonson, Boca Raton, FL (US)

(72) Inventor: Robert E. Simonson, Boca Raton, FL (US)

( * ) Notice: Subject to any disclaimer, the term of this patent is extended or adjusted under 35 U.S.C. 154(b) by 0 days.

(21) Appl. No.: 18/397,665

(22) Filed: Dec. 27, 2023

Related U.S. Application Data

(63) Continuation of application No. 18/104,612, filed on Feb. 1, 2023, now Pat. No. 11,857,431.

(51) Int. Cl.
  *A61F 2/44* (2006.01)
  *A61F 2/28* (2006.01)
  *A61F 2/30* (2006.01)

(52) U.S. Cl.
  CPC ............ *A61F 2/442* (2013.01); *A61F 2/2846* (2013.01); *A61F 2002/3071* (2013.01); *A61F 2002/4435* (2013.01)

(58) Field of Classification Search
  CPC ......... A61F 2/44–447; A61F 2002/4415–4495
  See application file for complete search history.

(56) References Cited

U.S. PATENT DOCUMENTS

| | | | |
|---|---|---|---|
| 4,341,206 A | 7/1982 | Perett et al. | |
| 5,015,247 A | 5/1991 | Michelson | |
| 5,180,382 A | 1/1993 | Frigg et al. | |
| 5,246,458 A | 9/1993 | Graham | |
| 5,324,290 A | 6/1994 | Zdeblick | |
| 5,364,399 A | 11/1994 | Lowery et al. | |
| 5,549,612 A | 8/1996 | Yapp | |
| 5,591,235 A * | 1/1997 | Kuslich | A61B 17/701 606/279 |

(Continued)

FOREIGN PATENT DOCUMENTS

WO   WO 2010063111 A1   6/2010

OTHER PUBLICATIONS

Summary of Safety and Effectiveness FDA Approval Letter Apr. 2, 2001. pp. 1-8 Published Mar. 3, 2003 (Year: 2003).*

(Continued)

*Primary Examiner* — Matthew J Lawson
(74) *Attorney, Agent, or Firm* — Weisberg I.P. Law, P.A.

(57) ABSTRACT

A method of performing a transcorporeal procedure including placement of a vertebral body replacement device into a transcorporeal void within a cervical spine is disclosed. The method includes creating a working channel through a vertebral body of a vertebra by removing at least a portion of the vertebral body of the vertebra, beginning anteriorly and extending inwardly toward the epidural space, the working channel extending from an anterior wall through a posterior wall, and placing the vertebral body replacement device within the working channel, the placement of the vertebral body replacement device leaving the inferior and superior endplates to perform their function and leaving at least a portion of the intervertebral disc functional thereby avoiding an intervertebral fusion to an adjacent vertebra.

17 Claims, 4 Drawing Sheets

(56) References Cited

U.S. PATENT DOCUMENTS

| | | | |
|---|---|---|---|
| 6,015,436 A * | 1/2000 | Schonhoffer | A61F 2/44 623/17.11 |
| 6,149,686 A | 11/2000 | Kuslich et al. | |
| 6,248,110 B1 | 6/2001 | Reiley | |
| 6,419,705 B1 | 7/2002 | Erickson | |
| 6,436,102 B1 | 8/2002 | Ralph et al. | |
| 6,517,544 B1 | 2/2003 | Chelson | |
| 6,679,886 B2 | 1/2004 | Weikel et al. | |
| 7,094,239 B1 | 8/2006 | Michelson | |
| 7,128,760 B2 | 10/2006 | Michelson | |
| 7,160,304 B2 | 1/2007 | Michelson | |
| 7,226,481 B2 | 6/2007 | Kuslich | |
| 7,303,565 B2 * | 12/2007 | Buttermann | A61B 17/025 606/86 R |
| 7,803,188 B2 | 9/2010 | Justis et al. | |
| 7,867,263 B2 | 1/2011 | Lowry | |
| 7,905,885 B2 | 3/2011 | Johnson et al. | |
| 8,163,021 B2 | 4/2012 | Lowry | |
| 8,425,569 B2 | 4/2013 | O'Farrell | |
| 8,475,533 B1 * | 7/2013 | Castro | A61F 2/44 623/17.11 |
| 8,879,934 B2 | 11/2014 | Kameda | |
| 8,979,934 B2 | 3/2015 | Kirshman | |
| 9,044,338 B2 | 6/2015 | Schaller | |
| 9,962,166 B1 * | 5/2018 | Sachs | A61F 2/30744 |
| 10,064,735 B1 * | 9/2018 | Simonson | A61F 2/447 |
| 10,137,000 B1 * | 11/2018 | Simonson | A61B 17/7074 |
| 10,751,192 B1 | 8/2020 | Simonson et al. | |
| 11,000,290 B1 | 5/2021 | Sachs et al. | |
| 11,083,593 B1 | 8/2021 | Simonson et al. | |
| 11,523,912 B1 | 12/2022 | Simonson et al. | |
| 2001/0056302 A1 | 12/2001 | Boyer et al. | |
| 2002/0068974 A1 | 6/2002 | Kuslich | |
| 2003/0004575 A1 | 1/2003 | Erickson | |
| 2003/0065396 A1 | 4/2003 | Michelson | |
| 2003/0125747 A1 | 7/2003 | Sproul | |
| 2003/0181982 A1 | 9/2003 | Kuslich | |
| 2003/0195518 A1 | 10/2003 | Cragg | |
| 2006/0111714 A1 | 5/2006 | Foley | |
| 2007/0179610 A1 * | 8/2007 | Biedermann | G02F 1/13439 623/16.11 |
| 2009/0076555 A1 | 3/2009 | Lowry et al. | |
| 2009/0240334 A1 | 9/2009 | Richelsoph | |
| 2010/0152793 A1 * | 6/2010 | Lowry | A61B 17/1757 606/86 R |
| 2012/0316653 A1 * | 12/2012 | Ullrich, Jr. | A61F 2/4465 623/17.16 |
| 2016/0374819 A1 | 12/2016 | Ballard | |

OTHER PUBLICATIONS

FDA 510 Approval Ulrich Mailed on May 26, 2021. pp. 1-19 (Year: 2021).*

European Spine Journal, Jan. 3, 2007, Gun Choi et al.

510(k) premarket notification of intent to market and device description of Skyline® Anterior Cervical Plate System, Uniplate® Anterior Cervical Plate System, and Uniplate® 2 Anterior Cervical Plate System, Jul. 25, 2013, Submitted by Medos International Sàrl, Switzerland, DePuy Spine, Inc., Raynham, Massachusetts and Kirsten Lehmuller, Raynham, Massachusetts.

Summary of Safety and Effectiveness, Cervical Interbody Fusion Instrumentation, BAK/Cervical (BAK/C) Interbody Fusional System, Jan. 19, 2001.

Ulrich Medical USA; Ulrich Small Vertebral Body Replacement Product Brochure; Plano, TX; Oct. 2022; consisting of 4 pages.

Kavlock-S, K.D., U.S. Food & Drug Administration letter to Ulrich GmbH & Co. KG including Indications of Use; Nov. 1, 2019; consisting of 5 pages.

* cited by examiner

METHOD AND APPARATUS FOR PLACEMENT OF A VERTEBRAL BODY REPLACEMENT DEVICE INTO A TRANSCORPOREAL VOID DURING A SURGICAL OPERATION ON THE CERVICAL PORTION OF THE SPINE

CROSS REFERENCE TO RELATED APPLICATIONS

This application is a Continuation of U.S. patent application Ser. No. 18/104,612, filed on Feb. 1, 2023, which is incorporated herein by reference in its entirety.

FEDERALLY SPONSORED RESEARCH OR DEVELOPMENT

Not applicable

TECHNICAL FIELD

The present disclosure relates to vertebral body replacement devices and to using a vertebral body replacement device as an implant in the cervical spine for the purpose of placement within a transcorporeal void created in a vertebral body in the cervical spine during or after a surgical procedure.

BACKGROUND

In the spine, a motion segment includes the intervertebral disc and associated anatomy and the two adjacent vertebrae all of which allows for the movement that takes place between two vertebrae. A vertebral body replacement device eliminates the movement of a spinal motion segment.

The natural motion that occurs between vertebrae is what allows natural twisting and turning movements humans perform every day and rarely give any thought to. Located between two vertebrae is an intervertebral disc. This disc resides between the two vertebral bodies separating the bodies and allows for movement. The intervertebral disc is a critical component of what makes up a joint complex between two vertebrae. Anteriorly, the joint complex includes in part, the disc, the anterior longitudinal ligament and the endplates. Posteriorly, it includes the facets, pedicles, lamina, neural foramen, ligaments, and more. The joint complex is actually quite complex and it is functionally eliminated when a vertebral body replacement device is used. In the past, when a vertebral body replacement device was used in the cervical spine it was always placed between at least two individual adjacent vertebrae, filling the space of at least one removed intervertebral disc and often filling the space of at least a removed intervertebral disc and a portion of one or more vertebrae, thus resulting in the elimination of the motion of the subject disc joint complex.

In the field of orthopedic or neurological surgery of the spine, the vocabulary that can be used is intentionally descriptive. Specific words have very precise meanings. It is important that a surgeon, reading the post-operative notes from a procedure performed on a patient by another surgeon, can clearly understand exactly what was done during the course of the surgery previously performed. Additionally, regulatory agencies of the government want a very precise understanding of the devices they regulate and how such devices are used. This is accomplished by a very clear understanding of precise terms.

This also applies to implants for placement into the spine. In order for an implant to be called by a particular name, the implant must meet all the requirements placed upon an implant of that name. For example, for an implant to be called a Vertebral Body Replacement ("VBR") device, the implant will have to undergo very extensive testing often by an independent lab, in order to meet the requirements set out by the United States Food and Drug Administration (FDA) in order to qualify for the term VBR device.

When a device manufacturer uses the term VBR device, a surgeon will know the device has passed all the requirements to meet the definition of that term. The FDA will not allow a device to be referred to as a Vertebral Body Replacement device if the device has not been previously cleared for use by the FDA as fulfilling all the requirements laid out by the FDA. These requirements include among others mechanical testing, biocompatibility analysis, design features, labeling, etc. The penalties for calling a device by a name not previously cleared by the FDA are quite severe. If a device is going to be called a VBR device, the FDA must agree in advance that the device has passed the testing requirements laid out for a device to meet that definition. Improper labeling is not permitted.

The FDA and therefore also the industry will sometimes refer to devices by three letter codes that replace device terms. Outside of regulatory or manufacturing professionals these three letter codes are not commonly used around the general medical community or the general public, usually to avoid confusion for people outside of the industry. But within the regulatory or medical device field use of the three letter codes is common. These codes can be used to distinguish a limitation the FDA has placed on a device they have cleared as a Vertebral Body Replacement device. For example, a VBR device may be cleared for use in the cervical spine but not the lumbar spine. Such a VBR device cleared for use in the cervical spine is given the product code: PLR.

For example, the FDA provides the following as part of the definition and description for a PLR Vertebral Body Replacement device:
  Device—Spinal Vertebral Body Replacement device-Cervical
  Regulatory Description—Spinal intervertebral body fixation orthosis
  Definition—Vertebral Body Replacement in the cervical spine

SUMMARY

Disclosed herein is an inventive method of using a specific type of implant called a Vertebral Body Replacement device or a "VBR device," as an implant in a surgical procedure to be placed between the two endplates of a single vertebra of the cervical spine. This is in direct contrast to the common placement of a VBR device between the endplates of more than one vertebra.

The disclosed method of placement has not been performed heretofore and the use of such an implant for this procedure is counterintuitive for many reasons. Disclosed herein is a device that is capable of being placed within the confines of a single vertebra, thus preserving the motion.

Historically, use of a Vertebral Body Replacement device has necessarily meant placing the device between two or more vertebrae replacing a portion of, or all of, a vertebral body which necessarily eliminates the motion of those vertebrae. Removing an intervertebral disc and placing a VBR device into the space created by the removal of the intervertebral disc eliminates the functional capability of the motion segment. In its usual function, the VBR device provides the function of fixing two vertebrae in place thus eliminating motion. Eliminating motion is a characteristic of a typical VBR device. A transcorporeal procedure preserves the intervertebral disc and thus preserves motion. Therefore, disclosed herein is a method of using an implant designed for motion elimination and instead using the implant for a motion preservation procedure.

Placement of a VBR device into a transcorporeal void is not an intervertebral application which is the only application vertebral body replacement devices have been previously used and designed for.

For the purposes of this disclosure, the term "cervical spine" will follow the usual guidance of the FDA which when referring to Vertebral Body Replacement devices for the cervical spine, the term cervical includes the second vertebra (C2) through the first vertebra of the thoracic spine (T1). This is commonly expressed as (C2-T1) which means the second through seventh cervical vertebrae and the first and most superior of the thoracic vertebrae. In the present disclosure, unless otherwise specified, the term "device" is used interchangeably with the term "implant."

In one aspect of the present disclosure, a method of placing a Vertebral Body Replacement device between two vertebral endplates of a vertebra in a cervical spine is disclosed. The method includes creating a void in a vertebra of the cervical spine between the two endplates of the vertebra, and placing the Vertebral Body Replacement device into the void created between the two endplates of the vertebra.

According to one embodiment of this aspect, the method further includes providing a series of Vertebral Body Replacement devices, and selecting at least one Vertebral Body Replacement device from the series of Vertebral Body Replacement devices to place into the void between the two endplates. According to another embodiment of this aspect, the method further includes providing a plurality of Vertebral Body Replacement devices for placement into the cervical spine, wherein at least one of the plurality of Vertebral Body Replacement devices has dimensions different from other Vertebral Body Replacement devices, selecting at least one Vertebral Body Replacement device from the plurality of Vertebral Body Replacement devices, and placing the selected at least one Vertebral Body Replacement device into the cervical spine. According to another embodiment of this aspect, the Vertebral Body Replacement device includes a space for placement of bone graft therein.

According to one embodiment of this aspect, the method further includes providing a series of Vertebral Body Replacement devices, and selecting at least one Vertebral Body Replacement device from the series of Vertebral Body Replacement devices to place into the void between the superior endplate and the inferior endplate. According to another embodiment of this aspect, the method further includes providing a plurality of Vertebral Body Replacement devices for placement into the cervical spine, wherein at least one of the plurality of Vertebral Body Replacement devices has dimensions different from other Vertebral Body Replacement devices, selecting at least one Vertebral Body Replacement device from the plurality of Vertebral Body Replacement devices, and placing the selected at least one Vertebral Body Replacement device into the cervical spine. According to another embodiment of this aspect, the Vertebral Body Replacement device includes a space for placement of bone graft therein.

In another aspect, a method of placing an implant into a transcorporeal void created in at least one vertebra of the cervical spine is disclosed. The method includes creating a void in a vertebral body of the at least one vertebra, the void beginning anteriorly and directed posteriorly creating an exit at a back of the vertebral body, and placing the implant into the void between a superior endplate and an inferior endplate of the at least one vertebra, the implant being a vertebral body replacement device. In one embodiment of this aspect, during and after placement of the implant, the superior endplate and the inferior endplate of the at least one vertebra remain functionally intact. In another embodiment of this aspect, the vertebral body replacement device has been given a PLR product code from the Food and Drug Administration (FDA).

In another aspect, a method of performing a transcorporeal procedure including placement of a Vertebral Body Replacement device into a transcorporeal void within a cervical spine is provided. The method includes creating a working channel through a vertebral body of a vertebra by removing at least a portion of the vertebral body of the vertebra, beginning anteriorly and extending inwardly toward the epidural space, the working channel extending from an anterior wall through a posterior wall, and placing the Vertebral Body Replacement device within the working channel, the placement of the vertebral body replacement device leaving the inferior and superior endplates to perform their function and leaving at least a portion of the intervertebral disc functional thereby avoiding an intervertebral fusion to an adjacent vertebra.

In one embodiment of this aspect, the method further includes providing a series of Vertebral Body Replacement devices, and selecting at least one Vertebral Body Replacement device from the series of Vertebral Body Replacement devices to place into the void between the superior endplate and the inferior endplate.

In another embodiment of this aspect, the method further includes providing a plurality of Vertebral Body Replacement devices for placement into the cervical spine, wherein at least one of the plurality of Vertebral Body Replacement devices has dimensions different from other Vertebral Body Replacement devices, selecting at least one Vertebral Body Replacement device from the plurality of Vertebral Body Replacement devices, and placing the selected at least one Vertebral Body Replacement device into the cervical spine. In another embodiment of this aspect, the Vertebral Body Replacement device includes a space for placement of bone graft therein.

Disclosed herein is the inventive method of placing a Vertebral Body Replacement device into a transcorporeal void created in a vertebra of the cervical spine.

Also disclosed is a Vertebral Body Replacement device for placement into a transcorporeal void in the cervical spine.

Also disclosed herein is an inventive method of placing a Vertebral Body Replacement device into a transcorporeal void created in a vertebra of the cervical spine wherein the Vertebral Body Replacement device has a PLR product code.

What is described herein is a description of a specific type of implant that must meet exacting criteria in order to meet the FDA's standards as a VBR device or PLR device.

The methods described herein disclose the adaptation and or adoption and use of a device that meets all the criteria for, and qualifies as, a VBR device, for the use as an implant for placement within a transcorporeal void created in the cervical spine.

DETAILED DESCRIPTION OF THE INVENTION

Figure 1:
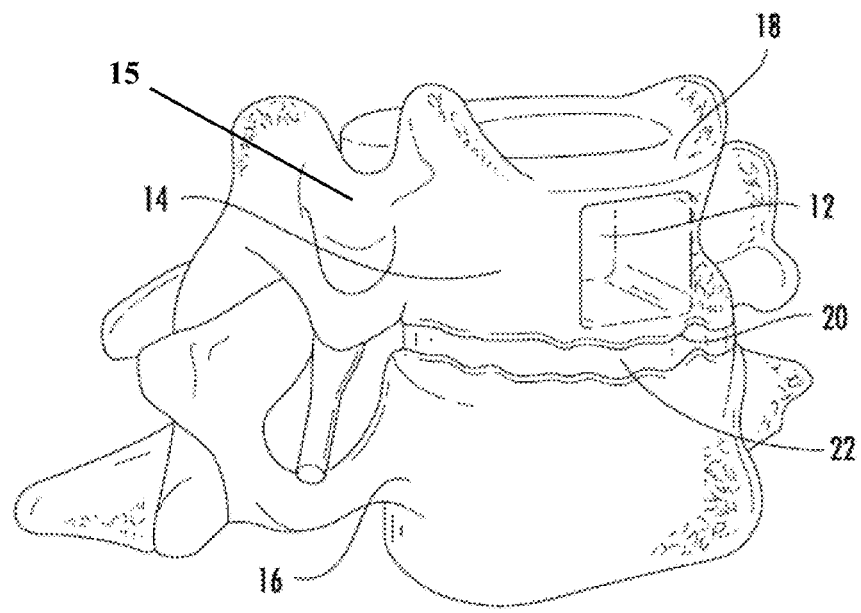
FIG. 1 illustrates a void created within a single vertebra for acceptance of a VBR implant therein.

As discussed above, a procedure described as a transcorporeal procedure in the cervical spine, also known as an intravertebral corpectomy, has a specific definition. While the definition does not change, some people use the additional terms: single-level partial vertebral body replacement, and/or partial replacement of a vertebral body, and/or partial vertebrectomy. By any of these names, this is a procedure wherein a portion of a vertebra, referred to herein as a portion of the vertebral corpus or vertebral body, is removed and/or drilled through. In order to be referred to as an intravertebral corpectomy or a transcorporeal procedure, the process of removing a portion of the vertebral body begins anteriorly or anterolaterally upon the front half on a vertebral body and proceeds posteriorly or posterolaterally through the back half of the vertebral body creating an exit opening through the back wall of the vertebral body, thus creating a working channel to provide surgical access to the area behind the vertebral body.

In the present disclosure, the terms "anterior" and "posterior" with regard to the anatomy of a vertebral body in the cervical spine, can be used to refer to the anterior half of the vertebral body or the posterior half of the vertebral body. The working channel includes an entry point on the anterior half of the vertebral body and an exit point on the posterior half of the vertebral body creating a functional pathway through the vertebral body passing from the front of the vertebral body through the back of the vertebral body. The purpose of the transcorporeal procedure is to provide surgical access to the pathology that lies upon, in proximity to, or behind the vertebral body portion of a vertebra. Using the transcorporeal approach to gain access to the area behind the vertebral body, the surgeon creates a working channel. The area behind the vertebral body is sometimes referred to as the greater epidural space. This working channel represents a functional pathway from the front of the vertebra, through the vertebral body, which includes passing through a back wall of the vertebral body in order to gain functional surgical access to pathologies that lie behind the vertebral body or in the greater epidural space.

After the performance of a transcorporeal procedure, including the treatment of the pathology that the surgeon treated behind the vertebral body, the transcorporeal void which is the working channel, must either be left void or repaired with an implantable device. This application discloses repairing the void created in the process of performing the transcorporeal procedure by the method of placing a Vertebral Body Replacement device into the void made during the creation of the working channel. The Vertebral Body Replacement device of this application is also useful in other vertebral body replacement procedures as the device can be used to preserve motion with placement into a vertebral body of a single vertebra or it can be used to eliminate motion by placing the device between two vertebrae into the space of a removed intervertebral disc. Therefore, the implant of this disclosure can preserve motion by placement into a transcorporeal void or eliminate motion by placement between two vertebrae in the cervical spine.

FIG. 1 illustrates a void created within a single vertebra for acceptance of a VBR implant therein.

Figure 2A:
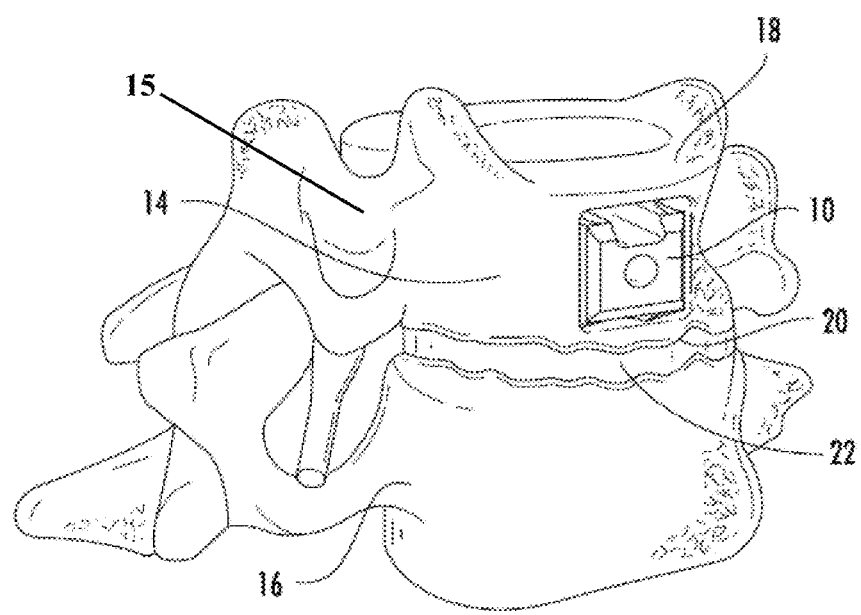
FIGS. 2A-2C illustrate the single vertebra after the insertion of the VBR implant between two endplates.
Figure 2B:
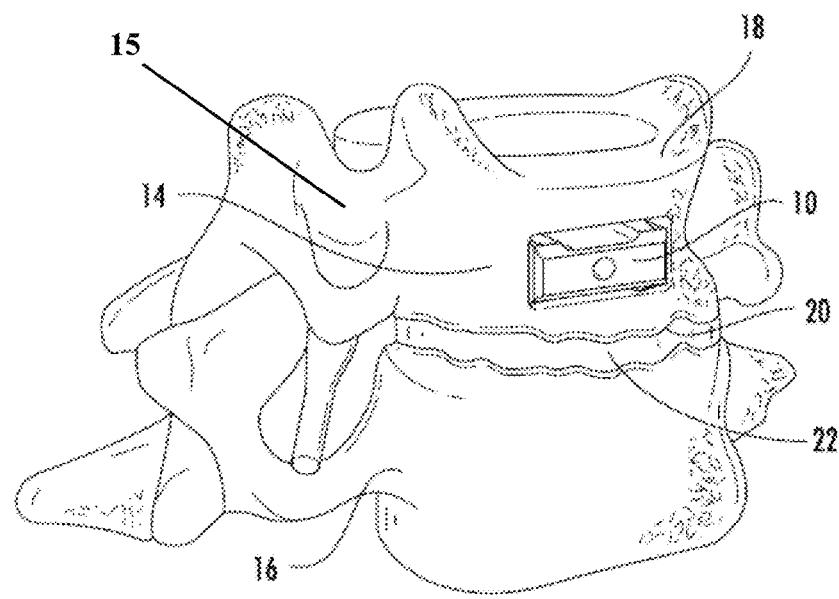
Figure 2C:
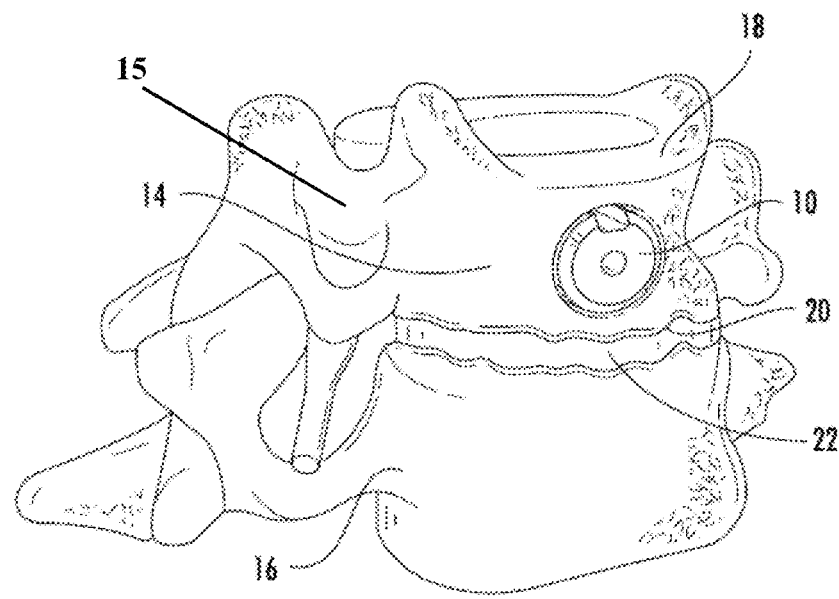

FIGS. 2A-2C illustrate the single vertebra after the insertion of the VBR implant between two endplates. FIGS. 2A, 2B, and 2C, each show a VBR device or implant inserted within a transcorporeal void of a single vertebra, where each VBR device is of a different size and/or dimension.

Figure 3A:
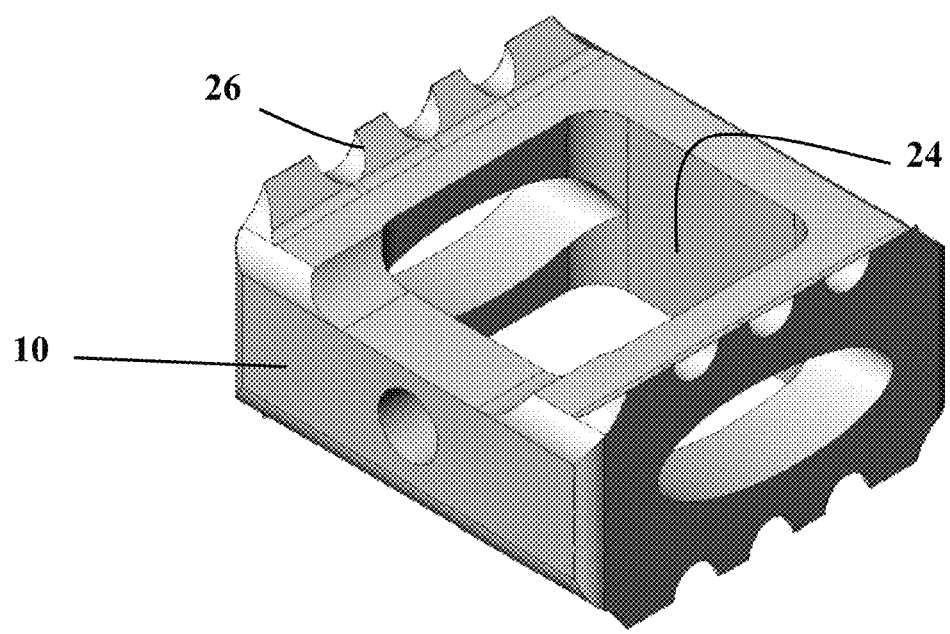
FIGS. 3A-3C illustrate alternate versions of the VBR implant showing a space therein for receiving bone graft.
Figure 3B:
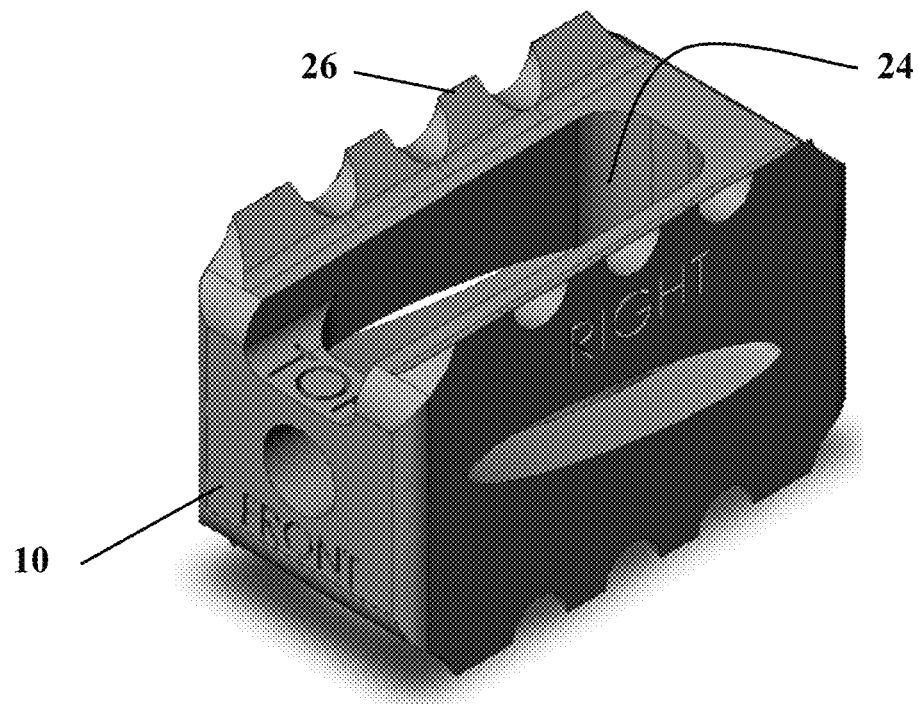
Figure 3C:
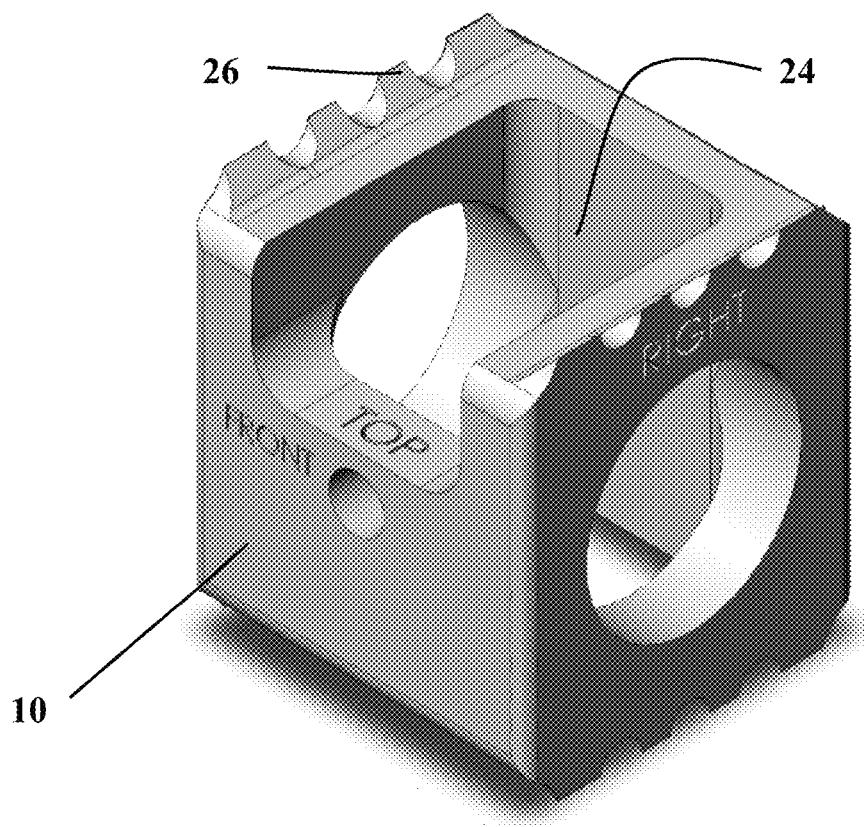

FIGS. 3A-3C illustrate alternate versions of the VBR implant showing a space therein for receiving bone graft.

The figures show an implant that represents the method of the placing of a Vertebral Body Replacement device into a void created in a vertebral body within a single vertebra of the cervical spine. The actual features of the Vertebral Body Replacement device will vary based upon anatomical needs and requirements of surgeons, patients, and regulatory bodies.

Referring to FIGS. 1 and 2A-2C, disclosed herein is a method of performing a transcorporeal procedure including placement of a Vertebral Body Replacement ("VBR") device 10 into a transcorporeal void 12 within a cervical spine (not shown), the method includes creating a working channel through a vertebral body 14 of a vertebra 15, beginning anteriorly and extending inwardly toward the epidural space. Herein, the "corpus portion of the vertebra 15" may also be referred to as the vertebral body 14. A working channel through which surgery can be performed is formed when the transcorporeal void 12 is completed. The working channel extends from an anterior wall through a posterior wall. The Vertebral Body Replacement device 10 is placed within the working channel, the placement of the Vertebral Body Replacement device 10 leaving the superior endplate 18 and inferior endplate 20 to perform their function and leaving at least a portion of the intervertebral disc 22 functional thereby avoiding an intervertebral fusion to an adjacent vertebra 16.

In the present disclosure, the terms "void" or "defect," with regard to transcorporeal surgery, can be used to refer to the surgically created space within or through a vertebral body 14. It is possible that a surgeon will perform a transcorporeal procedure upon more than one vertebra 15, but in such a case, each vertebra 15 would receive a VBR device 10 to repair the surgically created transcorporeal void 12. This is unlike traditional use of a VBR device 10 in which a VBR device 10 is used to span across multiple vertebrae.

In one embodiment, a method of placing an implant into a surgically created void in the spine is disclosed, the method including creating a void 12 in a vertebral body 14 of a cervical vertebra 15, the void 12 beginning anteriorly and directed posteriorly, creating an exit at the back of the vertebral body 14, and placing the implant into the void 12 between a superior endplate 18 and an inferior endplate 20 of the vertebra 15, the implant being a Vertebral Body Replacement device 10.

In another embodiment, a method of placing an implant into a surgically created void 12 in the spine is disclosed, the method including creating a void 12 in a vertebral body 14 of a cervical vertebra 15, the void 12 beginning anteriorly and directed posteriorly creating an exit at the back of the vertebral body 14, and placing the implant into the void 12 below the superior endplate 18 and above the inferior endplate 20 of the vertebra 15, the implant being a Vertebral Body Replacement device 10.

The afore-mentioned greater epidural space includes the spinal canal and its contents, the neural foramen, and all the ligamentous and neural tissues such as the spinal cord, nerve roots, and intervertebral discs, among other tissues. The goal of the transcorporeal procedure is to surgically treat a spinal problem that is causing the patient to suffer and at the same time preserve the motion segment. In the spine, a motion segment, which includes an intervertebral disc 22 allows the movement that takes place between two adjacent vertebrae, i.e., 15 and 16. The disc 22 sits between the two adjacent vertebrae 15 and 16, separating the bodies and allowing for movement.

The goal of the transcorporeal procedure is to address the pathology by going through the vertebral body 14, between the superior endplate 18 and inferior endplate 20 of a single vertebral body 14 without eliminating the movement of the vertebra 15 by preserving the intervertebral disc 22 and the movement in allows. If a surgeon does not want to try to preserve the motion of the two vertebrae 15 and 16, the surgeon will not perform a transcorporeal procedure; the surgeon can simply remove the disc 22 that separates the two vertebrae 15 and 16 and access the pathology by going between the two vertebrae 15 and 16 through the now open space where the disc 22 was removed. In this case, the surgeon would now fuse the two vertebrae 15 and 16 together by using an implant, often a Vertebral Body Replacement device 10, placed between the endplates of two vertebrae 15 and 16 thus eliminating the motion segment.

While the transcorporeal procedure has been thoroughly documented to be successful and beneficial to the patient, the procedure has failed to get widespread acceptance. One of the reasons for this lack of acceptance is due to a lack of implants available to repair the working channel or void created in the process of gaining access to the greater epidural space by working through a vertebral body.

Disclosed herein is an inventive method of using a specific class of implant called a Vertebral Body Replacement (or "VBR") device 10 as the implant to be placed into a transcorporeal void 12, which is also referred to herein, when completed, as a working channel. The VBR devices 10 are from a category of implants that are associated with intervertebral use. This is what one would intuitively consider to be the opposite of a transcorporeal procedure. Intervertebral use means the devices are placed between at least two vertebrae 15 and 16. VBR devices 10 are implants that are typically associated with the fusion of two or more vertebrae 15 and 16 after removing an intervertebral disc 22 and some of the bone of at least one or more vertebrae 15 and 16. What is common among VBR devices 10 is that this group of implants is typically associated with a fusion procedure which eliminates the motion between at least two vertebrae 15 and 16.

This is the opposite of the goal of performing a transcorporeal procedure. As stated earlier, the intent of a transcorporeal procedure is to avoid performing an intervertebral fusion so it is counterintuitive to look to the VBR intervertebral fusion device to perform a motion-preserving surgical procedure.

Disclosed herein is an inventive method of using a specific type of implant, a VBR device 10 that has not, heretofore, been used in conjunction with transcorporeal surgery or for use within a single vertebra 15. In accordance with the methods disclosed herein, the implant 10 may be placed for the filling, the repair, and or the support and healing of the transcorporeal void 12, i.e. working channel. This specific use of VBR 10, placed within a transcorporeal void 12 within a single vertebra 15, has not been done before because the use of such a VBR implant 10 is counterintuitive as explained herein.

VBR devices 10 are typically used as intervertebral implants, meaning they are implants that are engineered to succeed after being placed into an environment which carries significant compressive loads. These types of implants are typically placed between two vertebrae 15 and 16, or what remains of two vertebrae in the cervical spine after the removal of part of or all of an intervertebral disc 22 as well as a portion of, or all of, one, or both of the vertebrae 15 and 16 adjacent to the disc space. After placement between two vertebrae 15 and 16, all of the weight of the body above the implant 10 is compressing down upon the implant 10. VBR devices, including the VBR device 10 disclosed herein, may include "teeth" 26 (shown in FIGS. 3A-3C) or significant features of engagement to keep them from sliding or moving forward or backward. This compressive force allows the teeth of the implant 10 to press into the vertebra 15 above and the vertebra 16 below the implant 10 to provide engagement. During surgery, the surgeon distracts or holds the vertebrae 15 and 16 apart from one another. Distracting or holding the vertebrae 15 and 16 apart accomplishes two primary functions. The first is it enlarges the space between the vertebrae 15 and 16 providing greater access to the greater epidural space. Secondly, the enlarged space also importantly allows for the placement of the VBR device 10. A VBR device 10 is engineered not to slide or otherwise move within bone. During the traditional use of a VBR device 10, once the device 10 is placed into the open space between two vertebrae 15 and 16, the surgeon will release the distraction and allow the two or more vertebrae to compress down on the VBR device 10 creating engagement with the teeth pressing into the bone. This compression only increases as the patient stands up post operatively and gravity and the weight of the patient further compress the implant 10 between the vertebrae 15 and 16. This compression creates engagement that holds the implant 10 in place and facilitates healing through bone growth.

The teeth also prevent the implant 10 from being easily slid into a fixed, non-distracted void such as a transcorporeal void 12 that cannot be distracted apart. As a transcorporeal void 12 is created in a single vertebra 15, i.e., a single bone, the space cannot be distracted apart to make room for the VBR device 10 having a significant number (or size) of teeth to be slid into position when implanted. The size and design of the teeth, which provide features engineered to grasp and hold position to bone and not slide, have to be taken into consideration for use in a transcorporeal application. As described, a transcorporeal procedure requires the placement of the VBR device 10 within a void 12 made in the body of a single vertebra 15.

This disclosure of the method of placing a VBR device 10 into a transcorporeal void 12 is as mentioned counterintuitive for a number of reasons. One reason is the relationship between the implant 10 and the stability of the spinal segment. Currently, VBR devices 10 have been placed into unstable spinal segments of the cervical spine where a discectomy and partial or complete vertebrectomies have been performed. In these cases, the VBR device 10 is placed into an unstable spinal segment. The disclosed inventive method provides for a VBR device 10 to be placed into the transcorporeal void 12 in the vertebral body 14 portion of an individual vertebra 15 of the cervical spine. In such a case, the VBR device 10 performs in a spinal segment that does not have a lack of stability; the VBR device 10 must perform in a stable environment.

Further, using a VBR device 10 in the manner described herein is counterintuitive because VBR devices 10 are designed to take advantage of a characteristic of bone and bone growth referred to as Wolff's Law. Wolff's Law teaches that bone density changes in response to changes in the functional forces on the bone. In other words, Wolff's Law teaches that bone grows when stress or pressure in applied to it. For example, this is the reason why regular exercise is vital to maintaining bone mass and strength throughout life and it is also for example, a challenge to astronauts who spend significant time in low gravity environments. Without loads, bone begins to weaken, while with loads bone begins to strengthen and grow. This is one of several reasons why the placement of a VBR device 10 into the vertebral body 14 of a single vertebra 15 has not been attempted. Traditional analysis teaches that a VBR device 10 placed into a transcorporeal void 12 will not have an adjacent vertebra 16 to press into in order to be fully and formally loaded to function as intended.

VBR devices 10 are designed to carry and function and heal growing bone under a load and this load is an important part of the healing process as it stimulates new bone growth. This intervertebral load is not available to a VBR device 10 placed into a transcorporeal void 12. Therefore bone growth has to be achieved via other assisting mechanisms. Placement of a VBR device 10 into a single vertebra 15 instead of between two vertebrae 15 and 16 under load is, with initial analysis, in contrast to Wolff's Law of bone growth and other principles that relate to bone growth and Vertebral Body Replacement devices 10.

The implant of the present disclosure is a VBR device 10 that is placed between the internal aspects of the endplates of a single vertebra 15, i.e., into the body or created defect in a vertebra 15, below the superior endplate 18 and above the inferior endplate 20 of one vertebra 15. This is different than intervertebral surgeries. Phrased differently, the method of the present disclosure includes placing a VBR device 10 into the vertebral body 14 of one vertebra 15 to fill a transcorporeal defect or hole. By contrast, prior to this disclosure, a VBR device 10 was placed only between two vertebrae 15 and 16 replacing a removed intervertebral disc 22. When an intervertebral disc 22 is removed and replaced by an implant for fusion, the vertebral endplates in contact with the implant are no longer functionally intact. This means the endplates are no longer interfacing with an intervertebral disc 22 but are interfacing with a fusion implant. Thus, bone is growing into the fusion implant eliminating the motion and the traditionally healthy function of a vertebral endplate.

Disclosed herein is the method comprising creating a void 12 in a vertebral body 14 of a cervical vertebra 15, the void beginning anteriorly and directed posteriorly, creating an exit at a posterior aspect of the vertebral body 14 and placing an implant into the void 12 between a superior endplate 18 and an inferior endplate 20 of the vertebra 15, the implant being a Vertebral Body Replacement device 10, leaving both endplates functionally intact.

The method of placing a VBR device 10 into a transcorporeal void 12 will necessarily require the VBR device 10 to function and promote bone growth and healing without the benefit of intervertebral compression.

This disclosure discloses a VBR device 10 to be used to repair and help heal a transcorporeal void 12 using the methods disclosed herein. An exemplary method is placing an implant into a transcorporeal void 12 created in at least one vertebra 15 of the cervical spine, the method including creating a void 12 in a vertebral body 14 of a vertebra 15, the void 12 beginning anteriorly and directed posteriorly creating an exit at the back of the vertebral body 14; and placing the implant into the void 12 between a superior endplate 18 and an inferior endplate 20 of the vertebra 15, the implant being a Vertebral Body Replacement device 10. The aforementioned methods described herein will allow the superior endplate 18 and the inferior endplate 20 of the vertebra 15 to remain functionally intact.

FIGS. 3A-3C illustrate alternate versions of the VBR implant 10 of the present disclosure. In each figure, space 24 is shown. Space 24 is configured to receive bone graft therein. Further, each figure illustrates a series of teeth 26 on both the top and bottom of implant 10. It should be noted that the placement, size, number, and dimension of teeth 26 shown in the figures is exemplary only, and the present disclosure is not limited to the placement, size, number, and dimension of teeth 26 shown in these figures.

As shown in the figures, one of a plurality of VBR devices 10 can be selected for placement into the cervical spine. In one or more embodiments, at least one of the plurality of VBR devices 10 has dimensions different from other VBR devices 10. The shape, size and dimensions of the VBR devices 10 shown in the figures are not meant to be limiting in any way and the method disclosed herein can use VBR devices 10 of shapes, sizes, and dimensions not necessarily depicted in the drawing figures.

The invention claimed is:

1. A method of placing a device into a vertebral body of a single vertebra in a cervical spine, the method comprising:
   placing the device into a void between two endplates of the single vertebra of the cervical spine during a performance of an anterior surgical procedure to the cervical spine, the device being cleared by the Food and Drug Administration (FDA) for use in the cervical spine, wherein the device being placed into the single vertebra of the cervical spine is an implant, and wherein placing of the device into the void leaves at least a portion of adjacent intervertebral discs functional thereby avoiding an intervertebral fusion to an adjacent vertebra.

2. The method of claim 1, further comprising:
   providing a series of devices; and
   selecting at least one device from the series of devices to place into the void in the vertebral body.

3. The method of claim 1, further comprising:
   providing a plurality of devices for placement into the cervical spine, wherein at least one of the plurality of devices has dimensions different from other devices;
   selecting at least one device from the plurality of devices; and
   placing the selected at least one device into the cervical spine.

4. The method of claim 1, wherein the device includes a space for placement of bone graft therein.

5. The method of claim 1, wherein when the device is placed within the void of the single vertebra, motion is preserved.

6. The method of claim 1, the placement of the device leaving a superior endplate and an inferior endplate of the single vertebra to perform their function and leaving at least a portion of an intervertebral disc functional thereby avoiding an intervertebral fusion to an adjacent vertebra.

7. A method of performing a partial vertebrectomy procedure including placement of an implantable device into a partial vertebrectomy void within a cervical spine, the method comprising:
   creating a working channel through a vertebral body of a single vertebra by removing at least a portion of the vertebral body of the single vertebra, beginning anteriorly and extending inwardly to provide surgical access; and placing the implantable device within the working channel, the placement of the implantable device leaving at least a portion of adjacent intervertebral discs functional thereby avoiding an intervertebral fusion to an adjacent vertebra, the implantable device being cleared by the Food and Drug Administration (FDA) for use in the cervical spine.

8. The method of claim 7, wherein the implantable device has been given a PLR product code from the (FDA).

9. The method of claim 7, wherein the implantable device is a Vertebral Body Replacement (VBR) device, the method further comprising:

providing a series of VBR devices; and selecting at least one VBR device from the series of VBR devices to place into the void.

10. The method of claim 7, wherein the implantable device is a Vertebral Body Replacement (VBR) device, the method further comprising:

providing a plurality of VBR devices for placement into the cervical spine, wherein at least one of the plurality of VBR devices has dimensions different from other VBR devices;

selecting at least one VBR device from the plurality of VBR devices; and placing the selected at least one VBR device into the cervical spine.

11. The method of claim 7, wherein the implantable device includes a space for placement of bone graft therein.

12. A method of placing a device cleared by the Food and Drug Administration (FDA) for use between two vertebrae of a cervical spine, the method comprising placing the device between two endplates of a single vertebra of the cervical spine during performance of an anterior surgical procedure to the cervical spine, wherein placing of the device between the two endplates leaves at least a portion of adjacent intervertebral discs functional thereby avoiding an intervertebral fusion to an adjacent vertebra.

13. A method of performing a partial vertebrectomy procedure upon at least one cervical vertebra during performance of an anterior cervical spinal surgical procedure, the method comprising:

placing an implant into a void created between two endplates of the at least one cervical vertebra, the void created by the performance of the partial vertebrectomy procedure, wherein the implant has been cleared by the Food and Drug Administration (FDA) for use in a cervical spine, and wherein placing of the implant into the void leaves at least a portion of adjacent intervertebral discs functional thereby avoiding an intervertebral fusion to an adjacent vertebra.

14. The method of claim 13, wherein during and after placement of the implant, the two endplates of the at least one cervical vertebra remain functionally intact.

15. The method of claim 13, wherein the implant is a Vertebral Body Replacement (VBR) device, the method further comprising:

providing a series of VBR devices; and selecting at least one VBR device from the series of VBR devices to place into the void.

16. The method of claim 13, wherein the implant is a Vertebral Body Replacement (VBR) device, the method further comprising:

providing a plurality of VBR devices for placement into the cervical spine, wherein at least one of the plurality of VBR devices has dimensions different from other VBR devices;

selecting at least one VBR device from the plurality of VBR devices; and placing the selected at least one VBR device into the cervical spine.

17. The method of claim 13, wherein the implant includes a space for placement of bone graft therein.

* * * * *